(12) United States Patent
Theodore et al.

(10) Patent No.: US 8,192,626 B2
(45) Date of Patent: ***Jun. 5, 2012

(54) WASTEWATER CHEMICAL/BIOLOGICAL TREATMENT METHOD FOR OPEN WATER DISCHARGE

(75) Inventors: Marcus G. Theodore, Salt Lake City, UT (US); Larry P. Wardle, Bountiful, UT (US)

(73) Assignee: Earth Renaissance Technologies, LLC, Salt Lake City, UT (US)

( * ) Notice: Subject to any disclaimer, the term of this patent is extended or adjusted under 35 U.S.C. 154(b) by 44 days.

This patent is subject to a terminal disclaimer.

(21) Appl. No.: 12/927,168

(22) Filed: Nov. 9, 2010

(65) Prior Publication Data

US 2012/0085705 A1 Apr. 12, 2012

Related U.S. Application Data

(63) Continuation-in-part of application No. 12/455,654, filed on Jun. 4, 2009, now Pat. No. 8,097,168, which is a continuation-in-part of application No. 12/286,083, filed on Sep. 26, 2008, now Pat. No. 7,566,400, which is a continuation-in-part of application No. 11/893,557, filed on Aug. 14, 2007, now Pat. No. 7,455,773.

(51) Int. Cl.
*C02F 3/00* (2006.01)

(52) U.S. Cl. ........ 210/620; 210/631; 210/724; 210/743; 210/749; 210/758

(58) Field of Classification Search .................. 210/620, 210/631, 724, 743, 749, 758
See application file for complete search history.

(56) References Cited

U.S. PATENT DOCUMENTS

| | | | |
|---|---|---|---|
| 3,493,328 A * | 2/1970 | Nieuwenhuis | 423/56 |
| 4,304,673 A | 12/1981 | Reynolds et al. | |
| 4,340,489 A | 7/1982 | Adams et al. | |
| 4,765,911 A | 8/1988 | Rasmussen | |
| 5,906,750 A | 5/1999 | Haase | |
| 6,881,339 B1 * | 4/2005 | Hogl et al. | 210/605 |
| 8,097,168 B2 * | 1/2012 | Theodore et al. | 210/724 |
| 2011/0148108 A1 * | 6/2011 | Ammon et al. | 285/417 |

OTHER PUBLICATIONS

Wikipedia, "Chemical oxygen demand".
Wikipedia, "Biochemical oxygen demand".

* cited by examiner

*Primary Examiner* — Chester Barry
(74) *Attorney, Agent, or Firm* — Marcus G. Theodore

(57) ABSTRACT

A wastewater treatment method employing chemicals for disinfection, and precipitation of suspended solids, heavy metals and phosphates before subsequent aerobic bacterial biological treatment using *Nitrosomonas* and *Nitrobacter* bacteria to remove ammonia and nitrates/nitrites and BOD compounds to produce recovered treated wastewater suitable for open water discharge.

8 Claims, 2 Drawing Sheets

WASTEWATER CHEMICAL/BIOLOGICAL TREATMENT METHOD FOR OPEN WATER DISCHARGE

CROSS REFERENCES TO RELATED APPLICATIONS

This application is a continuation-in-part patent application of the continuation-in-part application Ser. No. 12/455,654 filed Jun. 4, 2009 entitled "Wastewater Photo Biomass/Algae Treatment Method, now U.S. Pat. No. 8,097,168, which is a continuation-in-part of prior patent application Ser. No. 12/286,083 filed Sep. 26, 2008 entitled "Wastewater Chemical/Biological Treatment Recovery Method and Apparatus", now U.S. Pat. No. 7,566,400, which is a continuation-in-part of application Ser. No. 11/893,557, filed on Aug. 14, 2007, now U.S. Pat. No. 7,455,773.

BACKGROUND OF THE INVENTION

1. Field

This invention comprises a wastewater treatment method employing chemicals for disinfection, and precipitation of suspended solids, heavy metals and phosphates before subsequent aerobic bacterial biological treatment of the remaining nutrients using *Nitrosomonas* and *Nitrobacter* bacteria to remove ammonia, nitrates/nitrites, and BOD compounds to produce recovered treated wastewater suitable for open water discharge.

2. State of the Art

Various types of wastewaters are known. As used herein, it is principally directed to wastewaters containing organic and macronutrients suitable for growth of plants, algae, and biomass, including runoff from farmlands, domestic sewage from dwellings, business buildings, institutions, containing ground water, surface water, and/or storm water, and can include wastewater, having already undergone primary and secondary treatment according to conventional wastewater treatment plant processes. Consequently wastewater as used herein also includes other agricultural and industrial wastewaters containing similar nutrients and requiring similar conditioning, disinfection, and deodorizing to provide feedstock for growing *Nitrosomonas* and *Nitrobacter* bacteria.

One source of wastewater is that present in sewage treatment gathering systems, which are processed by various methods. Most large municipal systems employ a series of settling ponds sequentially concentrating the solids contained in wastewater either with or without polymers for separation from liquids via mechanical separation means, such as belt presses. To produce a clean effluent that can be safely discharged to watercourses, wastewater treatment operations use three or four distinct stages of treatment to remove harmful contaminants; according to the United Nations Environmental Programme Division of Technology, Industry, and Economics Newsletter and Technical Publications Freshwater Management Series No. 1, *"Bio-solids Management: An Environmentally Sound Approach for Managing Sewage Treatment Plant Sludge"*.

Preliminary wastewater treatment usually involves gravity sedimentation of screened wastewater to remove settled solids. Half of the solids suspended in wastewater are removed through primary treatment. The residual material from this process is a concentrated suspension called primary sludge, subsequently undergoing additional treatment to become bio-solids.

Secondary wastewater treatment is accomplished through a biological process, removing biodegradable material. This treatment process uses microorganisms to consume dissolved and suspended organic matter, producing carbon dioxide and other by-products. The organic matter benefits by providing nutrients needed to sustain the communities of microorganisms. As microorganisms feed, their density increases and they settle to the bottom of processing tanks, separated from the clarified water as a concentrated suspension called secondary sludge, biological sludge, waste activated sludge, or trickling filter humus. By breaking down the sludge, the wastewater system loses energy and increases carbon dioxide emissions.

Tertiary or advanced treatment is used when extremely high-quality effluent is required, including direct discharge to a drinking water source. The solid residual collected through tertiary treatment consists mainly of chemicals added to clean the final effluent, which are reclaimed before discharge, and therefore not incorporated into bio-solids. Tertiary or advanced treatment does not reduce the treated wastewater brine content, requiring energy intensive Quaternary brine treatment removal using reverse osmosis and distillation, and other methods.

Combined primary and secondary solids comprise the majority of material used at municipal plants for bio-solids production. Careful management throughout the entire treatment process allows plant operators to control the solids content, nutrient value and other constituents of bio-solids.

The Municipal Sludge-to-Bio-Solids Treatment Process

Three important factors must be addressed through further processing before this material can be utilized: (1) pathogen levels, (2) presence of potentially harmful industrial contaminants, and pharmaceuticals and personal care products, and (3) water content.

The principal process employed to convert municipal sludge into bio-solids is called stabilization. Stabilization accelerates the biodegradation of organic compounds, reduces the microbial population including pathogens, and renders the material microbiologically safe for some types of agricultural use. Biological stabilization uses aerobic or anaerobic treatment to reduce the organic content of solids through controlled biodegradation. Chemical stabilization does not reduce the quantity of biodegradable organic matter in solids, but creates process conditions inhibiting microorganisms, thereby slowing the degradation of organic materials and reducing odors. The most common chemical stabilization procedure is to elevate the pH level of the solids using lime or other alkaline materials. Thermal drying and composting can be used to stabilize bio-solids. Full pasteurization of bio-solids is not needed when the primary use is cropland application. Any potential risk to human health due to exposure to pathogens is eliminated through proper controlled application procedures and in-situ microbial decomposition.

The presence of contaminants in the sludge or bio-solids arising from industrial discharges is a more challenging problem and may be the deciding factor in determining the choice of a utilization disposal option. Put simply, many industries have habitually used the sewer system as a convenient and low-cost way to discharge hazardous wastes. The contaminants accumulate in the biomass and sludge, and can render the material unfit for any beneficial use. The most common options used for disposal of this contaminated material are landfill or incinerations, particularly where heavy metals or pathogens are still present in the sludge. The cost is usually borne by the municipality rather than the hazardous waste generator. Bio-solids utilization is a good, environmentally sustainable option when the wastewater is from municipal sources only, or when a fully enforced industrial pre-treatment and discharge control system is in place. The decision to select an environmentally sustainable approach to bio-solids management can be used very effectively to review and correct polluting practices up-stream that should not be taking place.

The final concern is the water content of the bio-solids product. Primary and secondary sludge generally contain no more than four percent solids, and the storage and transportation costs of this semi-liquid material limit the application to nearby farmland. Processes to remove water from solids, therefore, are common in bio-solids production. The simplest method for removing water is gravity thickening, involving concentration by simple sedimentation. Allowing sufficient time for solids to settle in tanks can increase suspended solids concentration to five or six percent. Thickening can include flotation processes, gravity drainage belts, perforated rotating drums, and centrifuges. Nothing is added to bio-solids during the gravity thickening processes.

Dewatering is another standard method of water removal in bio-solids production. Simple dewatering involves containment of wastewater solids in drying beds or lagoons, where gravity, drainage, and evaporation remove moisture. More often, dewatering involves mechanical equipment including filter presses, vacuum filters, and centrifuges. Mechanically dewatered solids typically contain between 20% and 45% solids. Finally, drying processes can be used to remove even larger volumes of water from bio-solids. Thermal drying with direct or indirect dryers followed by polarization can remove virtually all water and stabilize bio-solids to the point of full compliance with any regulatory requirement. This method is used where a viable commercial market exists for the pelletized product, and drying energy costs can be passed on.

Thus a particular wastewater treatment facility design is highly dependent upon the wastewater inflows and sludge composition and the discharge and treatment permitting restrictions and plant objectives. Oftentimes these plant designs employ thermophilic and other digestion processes to decompose the sludge as part of the separation process. For example, Haase, U.S. Pat. No. 5,906,750 issued May 25, 1999 discloses a method for dewatering of sludge previously digested by a thermophilic digestion process employing polymers. The polymers are extremely hydrophilic as they agglomerate fine particles for separation from the wastewater in the belt presses. This gelatinous mechanically separated mass is then usually land filled or admixed with other fuels for burning, and may contain significant pathogens and heavy metals. Once deposited and covered, these landfills do not breakdown rapidly. They comprise large deposits of unstable gelatinous soil, which acts as a breeding ground for pathogens. If these separated solids are treated with chlorine for pathogen kill, chlorinated carcinogens often result, creating a different environmental hazard.

The mechanically separated gray water by-product is usually not treated and is then used for agricultural application, or dumped into a body of water for dilution. If treated with chlorine to kill pathogens before land application or dumping, its usage for agricultural purposes is less than ideal as any residual chlorine acts as an herbicide.

In addition, mechanical sludge separation typically requires a large series of settling ponds with wastewater residence times therein typically from 24 to 48 hours, depending upon the weather and nature of the sludge processed. Typically, landfill and polymer costs represent approximately 30 percent of wastewater treatment costs. This long dwell time results in further concentrations of the brines.

Other mechanical filtration methods provide sludge separation, but require continual unplugging of the filters; generating significant ongoing costs of filter replacement and declining effectiveness as the filter becomes plugged with the separated solids.

Conventional mechanical sewage separation plants are thus designed to breakdown and separate the wastewater components, and vent $CO_2$ into the air. They also use competing bacterials, which may interfere with the propagation of photo biomass/algae, and are capital and energy intensive and have to be operated within environmental discharge and landfill permit constraints. Consequently, they are not routinely used as a nutrient source to propagate algae and photo biomass. They require significant upfront capital investment and may result in long term environmental clean-up and remediation costs. As urban populations being served grow and landfill costs increase, these plants seldom meet permitting constraints without significant upgrades in design, particularly with respect to pathogen gray water discharge and the negative impacts caused by mountains of gelatinous solids.

Other chemical wastewater treatment methods employ chemical agglomeration and disposal methods, such as Adams et al., U.S. Pat. No. 4,340,489 issued Jul. 20, 1982 wherein wastewater is treated with sufficient sulfurous acid to effectuate disinfection. Polymers and other separation methods are then employed to remove the solids. Reynolds et. al., U.S. Pat. No. 4,304,673 issued Dec. 8, 1981 is another wastewater treatment process employing chemicals to disinfect sewage sludge continuously in a similar manner as Adams et al. Rasmussen, U.S. Pat. No. 4,765,911, issued Aug. 23, 1988 is another two-stage chemical treatment process for treating aerobic or anaerobic sewage sludge. These chemical wastewater treatment methods are not package systems, use chemicals at concentrations, which retard biomass/algae production, rely heavily on the use of polymers, and do not address the issues of BOD's and ammonia in treated wastewater or brine disposal methods.

As fish require certain levels of oxygen in wastewater for survival, treated wastewaters must be free of oxidizable materials, which lower oxygen level below this level for open stream discharge. As stated in Wikipedia, any oxidizable material present in a natural waterway or in an industrial wastewater will be oxidized both by biochemical (bacterial) or chemical processes. The result is that the oxygen content of the water will be decreased. Basically, the reaction for biochemical oxidation may be written as:

Oxidizable material+bacteria+nutrient+$O_2$→$CO_2$+$H_2O$+ oxidized inorganics such as $NO_3$ or $SO_4$ Oxygen consumption by reducing chemicals such as sulfides and nitrites is typified as follows:

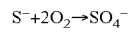

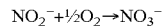

Since all natural waterways contain bacteria and nutrient, almost any waste compounds introduced into such waterways will initiate biochemical reactions (such as shown above). Those biochemical reactions create what is measured in the laboratory as the Biochemical Oxygen Demand (BOD).

Oxidizable chemicals (such as reducing chemicals) introduced into a natural water will similarly initiate chemical reactions (such as shown above). Those chemical reactions create what is measured in the laboratory as the Chemical Oxygen Demand (COD).

Both the BOD and COD tests are a measure of the relative oxygen-depletion effect of a waste contaminant. Both have been widely adopted as a measure of pollution effect. The BOD test measures the oxygen demand of biodegradable pollutants whereas the COD test measures the oxygen demand of biogradable pollutants plus the oxygen demand of non-biodegradable oxidizable pollutants. Hereinafter both BOD's and COD's will be referred to as BOD's.

Thus, there remains a need for a method and apparatus, able to be rapidly installed either as a standalone or retrofit package wastewater treatment system to chemically treat and recover wastewater solids and liquids for subsequent environmental biological usage and polishing. The treatment method described below provides such an invention suitable for first disinfecting and precipitating suspended solids, heavy metals and phosphates for filtration removal before using *Nitrosomonas* and *Nitrobacter* bacteria to remove ammonia and BOD's from the treated wastewater to produce recovered treated wastewater suitable for open stream discharge.

SUMMARY OF THE INVENTION

The present invention comprises a wastewater treatment method employing chemical dewatering and biological treatment technology for chemically disinfecting and precipitating suspended solids, heavy metals and phosphates for filtration removal before using *Nitrosomonas* and *Nitrobacter* bacteria to remove ammonia and nitrogen compounds and BOD's to produce recovered wastewater suitable for open stream discharge.

*Nitrosomonas* is a genus comprising rod shaped chemoautotrophic bacteria. *Nitrosomonas* bacteria oxidize ammonia into nitrite in their metabolic process. According to Wikipedia, *Nitrosomonas* are useful in treatment of industrial and sewage waste and in the process of bioremediation. They are important in the nitrogen cycle by increasing the availability of nitrogen to plants while limiting carbon dioxide fixation. The genus is found in soil, sewage, freshwater, and on building surfaces, especially in polluted areas that contains high levels of nitrogen compounds.

*Nitrosomonas* prefers an optimum pH of 6.0-9.0 and a temperature range of 20 to 30° C. Most species are motile with a flagellum located in the polar regions.

The bacteria have power generating membranes, which form long, thin tubes inside the cell, which use electrons from the oxidation of ammonia to produce energy. They obtain the carbon required from the atmosphere via carbon fixation, which converts carbon in a gaseous form into carbon bound in organic molecules.

Unlike plants, which fix carbon into sugar through energy gained through the process of photosynthesis, *Nitrosomonas* use energy gained through the oxidation of ammonia to fix gaseous carbon dioxide into organic molecules. *Nitrosomonas* must consume large amounts of ammonia before cell division can occur, and the process of cell division may take up to several days. This microbe is photophobic, and will cover itself in slime or form clumps with other microbes to avoid light.

The species *Nitrosomonas europaea* has been identified as also being able to degrade a variety of halogenated compounds including trichloroethylene, benzene, and vinyl chloride. Some *Nitrosomonas* species possess the enzyme, urease, which catalyzes the conversion of the urea molecule to two ammonia molecules and one carbon dioxide molecule. *Nitrosomonas europaea*, as well as populations of soil-dwelling ammonia-oxidizing bacteria, have been shown to assimilate the carbon dioxide released by the reaction to make biomass via the Calvin Cycle, and harvest energy by oxidizing ammonia (the other product of urease) to nitrite. This feature may explain enhanced growth of AOB in the presence of urea in acidic environments.

Some sources regard Nitrobacteraceae to be the family of the genus *Nicosomonas*.

*Nitrobacter*, according to Wikipedia is genus of mostly rod-shaped, gram-negative, and chemoautotrophic bacteria. *Nitrobacter* plays an important role in nitrogen cycle by oxidizing nitrite into nitrate in soil. Unlike plants, where electron transfer in photosynthesis provides the energy for carbon fixation, *Nitrobacter* use energy from the oxidation of nitrite ions, $NO_2^-$, into nitrate ions, $NO_3^-$ to fulfill their carbon requirements.

*Nitrobacter* have an optimum pH between 7.3 and 7.5, and will die in temperatures exceeding 120° F. (49° C.) or below 32° F. (0° C.). Some sources regard Nitrobacteraceae to be the family of the genus. *Nitrobacter*. Species in the genus *Nitrobacter* include *Nitrobacter winogradskyi*, *Nitrobacter hamburgensis*, *Nitrobacter vulgaris* and *Nitrobacter alkalicus*. According to Grundmann, *Nitrobacter* seem to grow optimally at 38° C. and at a pH of 7.9, but Holt states that *Nitrobacter* grow optimally at 28° C. and grows within a pH range of 5.8-8.5 and has an pH optima between 7.6 and 7.8. *Nitrobacter* belongs to the α-subclass of the Proteobacteria.

*Nitrobacter* may either be rod shaped, pear-shaped or pleomorphic. Cells normally reproduce by budding (Holt, 1993). Carboxysomes which aid carbon fixation are found in lithoautotrophically and mixotrophically grown cells. Additional energy conserving inclusions are PHB granules and polyphosphates. When both nitrite and organic substances are present, cells can exhibit biphasic growth, first the nitrite is used and after a lag phase, organic matter is oxidized. Chemoorganotrophic growth is slow and unbalanced thus more poly-β-hydroxybutyrate granules are seen that distort the shape and size of the cells.

*Nitrobacter* play an essential role in Aquaponics. *Nitrosomonas* bacteria first convert ammonia into nitrites. *Nitrobacter* convert the nitrites into nitrates, which are readily absorbed by the plants.

The present method uses modular equipment that can be rapidly installed at an existing wastewater treatment plant for chemical disinfection and removal of the suspended solids, heavy metals, and phosphates to condition treated wastewater for subsequent polishing in dark aerated open ponds via *Nitrosomonas* and *Nitrobacter* bacteria breakdown of the remaining ammonia compounds and BOD's in the recovered wastewater for open stream discharge.

Method

The method comprises chemically treating the wastewater containing solids, biomass/algae nutrients, and heavy metals with sulfur dioxide to condition the wastewater and separate the solids. The sulfurous acid, ($H_2SO_3$), dissociates to produce $H^+$, bi-sulfite ($HSO_3^-$), sulfite ($SO_3^=$), and free $SO_2$ species in solution, all hereinafter referred to as sulfurous acid. Conditioning the liquid fraction to kill competing bacteria and pathogens prevents loss of the nutrients and energy needed for growth of *Nitrosomonas* and *Nitrobacter* bacteria in a bioreactor. This also reduces the production of $CO_2$ by the competing bacteria and pathogens breaking down the nutrients.

Conditioning of the solids is defined as treating the filtered solids with sufficient $SO_2$ ensuring they will chemically dewater when allowed to drain, forming a fairly dry solid with a BTU content approximating wood chips or shavings. Conditioning of the solids generally results in a color change of the solids from a dark brown to a lighter gray brown color.

Before sulfurous acid treatment, the wastewater containing nutrients and solids may be aerated to kill viruses and oxidize unwanted chemicals. The subsequent sulfur dioxide treatment acts as a scavenger molecule to remove excess oxygen and act as a reducing agent to inactivate many unwanted pharmaceuticals and chemicals, which may affect subsequent bacteria growth. This oxidation/reduction cycle is particularly employed where pharmaceuticals and other drugs are present in the wastewater, which may affect bacteria production.

The $SO_2$ treated liquid wastewater fraction generally changes from a greenish color to a lighter gray brown colloidal suspension color. The malodorous smell of the raw wastewater is concomitantly replaced by a slight acidic smell. Consequently, the conditioning point can easily be determined by injecting more and more $SO_2$ into the wastewater until the color and odor changes occur—usually observed at a pH of approximately between 1.5 and 3.5, depending upon dwell time. If the color changes are too faint, the pH can be measured instead. Sulfur dioxide has lone electron pairs, allowing it to act as a Lewis base. Additionally it can act as a Lewis acid. The dissolved $SO_2$ gaseous content varies with temperature. For example, the grams/liter of dissolved sulfur dioxide in water at 20 degrees C. is 106.4 gm/L. It is 55.4 gm/L at 40 degrees. It is 32.5 gm/L at 60 degrees, and 21.3 gm/L at 80 degrees. Consequently, this sulfurous acid treated wastewater system with free $SO_2$/sulfurous acid/bi-sulfite/sulfite present in solution at a low pH forms a complex liquid/gas/solid phase chemistry system where reactions are difficult to describe and quantify exactly, but the above sulfurous acid wastewater conditioning endpoints are distinct. The conditioning of the wastewater and solids via oxidation/reduction reactions thus form self adhering solids, shedding water upon drying, and disinfected wastewater with high phosphate, BOD's and ammonia nitrate/nitrite nutrients at the point where the odor reduction and color changes of the conditioned solids and liquids occur. Heavy metals, in particular, are acid leached from the solids into the aqueous fraction, as nutrients, which if not removed can promote algae bloom or eutrophication. This leaves a heavy metals free separated solid suitable for land application or burning.

After sulfur dioxide-treatment, the chemically dewatered solids are separated and then disposed of consistent with applicable disposal permits. The resultant chemically treated wastewater liquid fraction is then neutralized with an alkaline reagent, such as lime, alum, calcium hydroxide, or calcium carbonate to raise the pH and inactivate the biocidal properties of the sulfurous acid at a pH between 6.0 and 9.0 suitable for raising *Nitrosomonas* and *Nitrobacter* bacteria. Use of alkaline reagents, precipitate the heavy metals as metal hydroxides. Some alkaline reagents such as lime, calcium carbonate, calcium hydroxide, aluminum sulfate and alum also precipitate phosphates present for filtration removal, leaving a disinfected ammonia, nitrate/nitrite nutrient rich recovered filtrate suitable for raising the *Nitrosomonas* and *Nitrobacter* bacteria. As *Nitrosomonas* and *Nitrobacter* bacteria require a pH of between 6.0 and 8.5, if higher pH levels are required for heavy metals removal sequential pH raising/lowering and filtration steps may be required, as some metal hydroxide precipitates re-dissolve as the pH is raised. For example, at higher pH levels, chromium and possibly iron and aluminum become more soluble as $Fe(OH)_4^-$ or $Al(OH)_4^-$ or $Cr(OH)_4^-$ ions. Thus, the filtered $SO_2$ treated liquid fraction of the treated wastewater has the pH raised to that required to precipitate and separate out the heavy metals and phosphates contained in the wastewater to produce a metal and phosphate free filtrate before finally lowering the pH to that required for *Nitrosomonas* and *Nitrobacter* bacterial treatment. This metals and phosphate precipitation process is generally conducted after suspended solids removal, where a metal free solid is required.

A pH of up to 11 may be required to precipitate all of the heavy metals as metal hydroxides. Some ammonia may be released at pH 11 to assist in ammonia removal. However, for most $SO_2$ treated wastewaters, the biological removal of ammonia and nitrates/nitrites via *Nitrosomonas* and *Nitrobacter* bacteria is sufficient. The *Nitrosomonas* and *Nitrobacter* bacteria are contained in a dark aerated bioreactor environment, such as the submersible opaque biofilm domes placed in open impoundments produced under the tradename Poo Gloo™ produced by Wastewater Compliance Systems, Inc. of Salt Lake City, Utah for removal of BOD's, ammonia and nitrates/nitrites, and some pharmaceuticals, as they grow. These concentric plastic half domes are separated with a growth media upon which the *Nitrosomonas* and *Nitrobacter* bacteria growth removes BOD's, ammonia, and nitrates/nitrites from water. A continuous source of air is circulated through these concentric half domes to circulate the water to be treated to expedite growth of these bacteria, while preventing algae growth in the darkened conditions. The two principle genera of *Nitrosomonas* and *Nitrobacter* bacteria remove ammonia nitrogen by oxidizing ammonium to nitrate with the intermediate formation of nitrite:

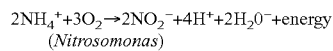
(*Nitrosomonas*)

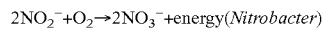

for an overall reaction of

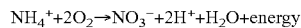

The nitrates/nitrites are then biologically removed consuming various nutrients in the wastewater via denitrifiers, which reduce nitrate to nitrite, and ultimately nitrite to nitrogen gas

for an overall reaction of

Thus not only do the denitrifying bacteria remove ammonia and nitrates/nitrites, they remove nutrients in the process reducing the BOD of the treated wastewater.

The optimum temperature for nitrifying bacteria is 28° C. to 36° C. For these fixed film bacteria, there is no growth at 0° C. or over 54° C. The optimum pH is between 8.3 and 9.3 with no growth below pH 6.7. The required dissolved oxygen is 4.6 mg/L per 1 mg/L $NH^+_4$—N, which is supplied with a continuous supply of air injected at the center of the bottom of the dome passing upward and out the top through a center passageway between the dome tops and out the discharge hole in the top of the outermost dome. This air circulation path also draws in water to be treated from the bottom the open pond through the media and out the discharge hole providing continuous pond circulation. The number of *Nitrosomonas/Nitrobacter* bioreactors is selected to provide the ammonia nitrate/nitrite and BOD removal levels required for open stream discharge.

The average $NH_4$—N removal is 1.5 mg/L or 0.54 lbs/day. The average BOD removal is 42 mg/L or 15 lbs/day. Assuming an average air flow rate through each Poo Gloo™ type bioreactors of 10 L/min there would be an average removal rate of 0.54 lbs/day/square foot $NH_4$—N, and BOD's of 15 lbs/day. These *Nitrosomonas/Nitrobacter* bioreactors effectively multiply the surface areas of open ponds over ten fold to speed the natural reactions of the *Nitrosomonas* and *Nitrobacter* bacteria to speed the nitrogen and BOD removal processes, resulting in a smaller open pond treatment plant footprint.

As these Poo Gloo™ type bioreactors remove BOD's along with ammonia and nitrates/nitrites, by removing first the suspended solids with the present method, a more expeditious effective removal rate of ammonia and nitrates/nitrites results as the *Nitrosomonas* and *Nitrobacter* bacteria can focus on the ammonia and nitrates/nitrites and not remove as many other nutrients.

When treating the incoming raw wastewater entering a sewage treatment plant, the resulting sulfur dioxide-treated, pH adjusted nutrients in wastewater are continuously generated, of a consistent composition, and provides a good source for *Nitrosomonas* and *Nitrobacter* cultivation, which consumes and removes the ammonia and nitrates/nitrites and BOD's. The *Nitrosomonas/Nitrobacter* bioreactors treatment process uses minimal oxygen circulation and thus generates carbon credits if more energy intensive SBR's and MBR's are placed on standby, and a recoverable wastewater for reuse.

The disinfection chemicals used for chemical dewatering are anhydrous or hydrous sulfur dioxide, which provide rapid water/solids separation. To minimize operator exposure to sulfur dioxide, preferably a sulfurous acid generator is employed. Sulfur dioxide chemical dewatering generates self-agglomerating solids, which can be more readily separated from the liquid fraction via conventional screens or drying beds without the need for polymers. Sulfur dioxide dissolves readily in water requiring little mixing. Disinfected sulfur dioxide separation of wastewater and dewatering of the resultant solids typically takes 20 minutes to an hour compared to the 24 and 48 hours separation time with present mechanical concentrators. The actual dwell time required is dependent upon the alkalinity of the wastewater, and the porosity of the separation equipment screens sand filters or bags employed. Generally, it is easier to move the solids in a 1% to 3% slurry, so the $SO_2$ may be injected into the wastewater and held the minimal time for the solids to reach the particle size in a pipeline or dwell tank to effectuate an initial separation for subsequent collection in an equipment filter screen, sand filter, or drain bag. The solids then further agglomerate and dewater more completely within the equipment screens, filters or bags. For those exceptional sludges, which may require initial agglomeration assistance, acid resistant polymers, such as cationic copolymers of acrylamide with a cationic monomer, or cationically modified acrylamide or polyamine, may be employed may be added to the sulfurous acidified wastewater. Other polyquaternary amines, which are pH insensitive and function well over a broad pH, may also be employed.

Because of the fast reaction time, the size of the treatment vessels and drain bags is materially less so land usage is minimized. Chemically treated wastewater methods provide greater flexibility in equipment separation designs, which result in further cost savings. Nor is there usually any need for adding polymers first to agglomerate the solids as is the case with conventional belt presses and centrifugal or mechanical separators used in conventional mechanical sewage treatment plants, providing additional cost savings.

Material handling costs are also reduced. Sulfur dioxide treatment generates an initial separated solid having a water content of 30% to 40% in approximately 5 to 10 minutes, depending on composition. These solids, after separation, are then allowed to continue to chemically dewater until a solids composition having water content as low as approximately 4% is effectuated. If the chemical exposure is extended to approximately 20 minutes to insure disinfection, odor generation during the remainder of the treatment and disposal process is avoided. Sulfur dioxide also acid leaches the heavy metals into the liquid fraction for ease of removal via the subsequent addition of lime.

This rapid sulfur dioxide injection and separation generating self-agglomerating solids and heavy metals in the liquid fraction enables the use of much smaller gas injection and separation equipment than conventional mechanical dewatering systems. The sulfur dioxide dewatering equipment can be installed in modules, as needed. Thus, sulfur dioxide dewatering requires lower capital equipment cost investment, and has comparable or somewhat higher handling costs.

Apparatus

Various embodiments of a wastewater treatment apparatus for disinfecting, removing heavy metals and phosphates, and suspended solids are described in the parent applications incorporated herein by reference, and also Ser. No. 12/798,088 filed Mar. 30, 2010 by John Harmon entitled "Method to Reduce Wastewater Treatment Plant Footprints and Costs. These apparatus produce a disinfected, demetalized and phosphate free filtrate, which then has the ammonia and nitrates/nitrites and BOD's removed as described above to provide a recovered treated wastewater suitable for open stream discharge.

DESCRIPTION OF THE ILLUSTRATED EMBODIMENTS

Figure 1:
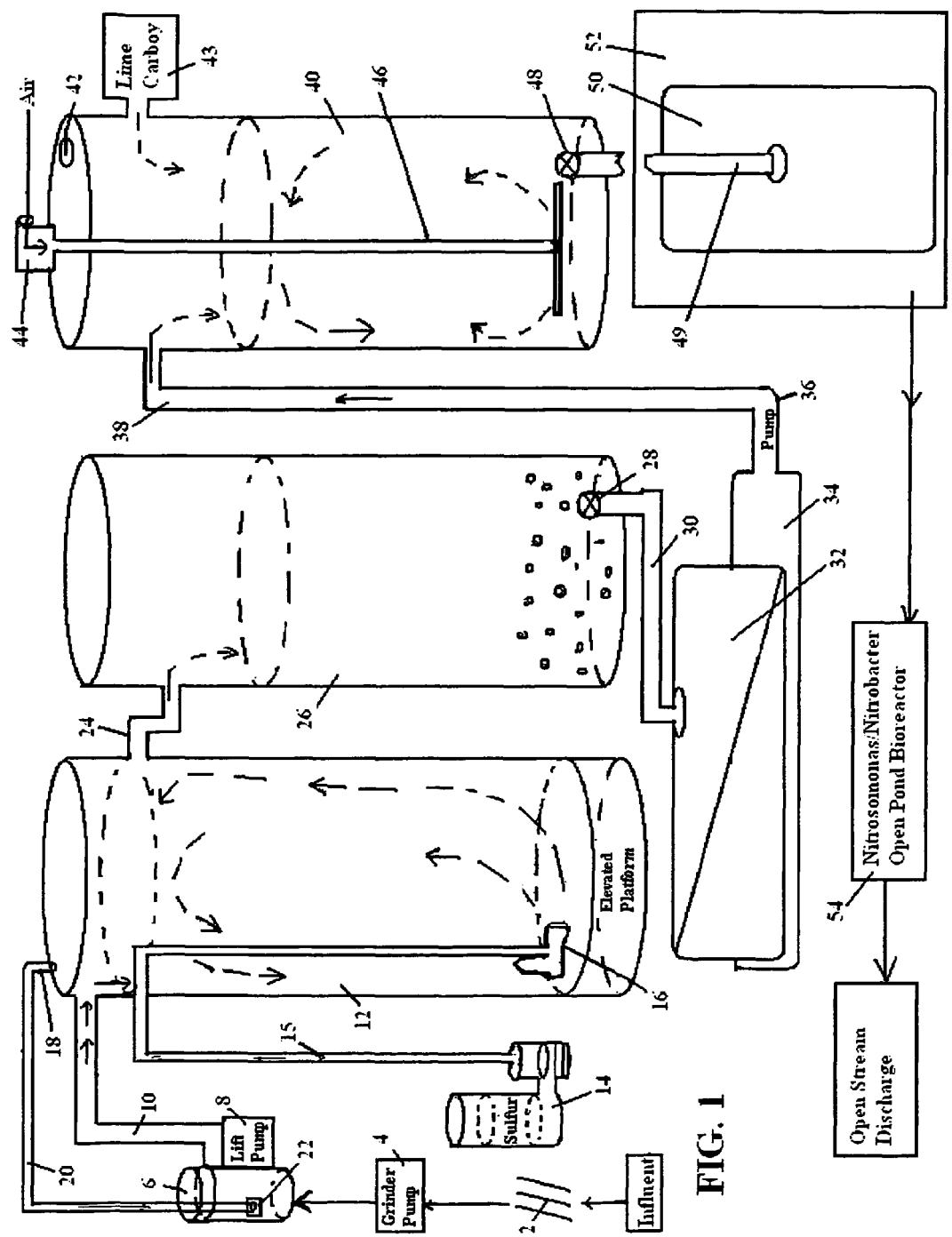
FIG. 1 illustrates a typical the layout of the wastewater treatment method.

FIG. 1 illustrates a typical layout of the wastewater treatment method disinfecting and adjusting the recovered treated wastewater for nitrogen removal before open stream discharge. The wastewater is screened with bar screens 2 to remove courser solids before grinding with a grinder pump 4 and passing into an open tank 5. There it is pumped with a lift pump 8 through a conduit 10 into an acid mixing tank 12. A sulfur dioxide generator 14 is connected with conduit 15 a jet aerator 16 drawing in air into the sulfur generator 14 to create sulfur dioxide for admixing into the screened wastewater by the jet aerator 16. The sulfur dioxide-treated screened wastewater is thoroughly saturated with sulfur dioxide and any excess bled off with a pressure relief outlet 18 to pass through a conduit 20 leading to an aspirator 22 to inject surplus sulfur dioxide into the entering influent.

The sulfur dioxide treated wastewater passes from the acid mixing tank 12 through a conduit 24 into a settling tank 26 where the solids agglomerate, heavy metals are acid leached from the solids into the liquid phase, and the liquids and solids are disinfected.

The sulfur dioxide-treated screened wastewater is then drained through valve 28 into a geotextile filter bag 32 associated with a collection reservoir 34 to separate the solids for disposal from the sulfur dioxide treated liquids containing disinfected heavy metals, phosphates, and ammonia and nitrates/nitrites.

The collected sulfur dioxide-treated liquids are then pumped via pump 36 through conduit 38 into a liming tank 40 fitted with a compressor 44 driving air mixer 46 to circulate lime from a lime carboy 43 to pH adjust the sulfur dioxide-treated liquids to precipitate heavy metals and phosphates at a pH required to grow *nitrosomonas*/and *nitrobacter* bacteria.

The pH adjusted sulfur dioxide-treated liquids are then passed through valve 48 via conduit 49 into another geotextile bag to separate the heavy metal and phosphate precipitates from the filtrate sent to a *Nitrosomonas/Nitrobacter* bioreactor 54 to remove the ammonia and nitrates/nitrites to a level suitable for open stream discharge.

Figure 2:
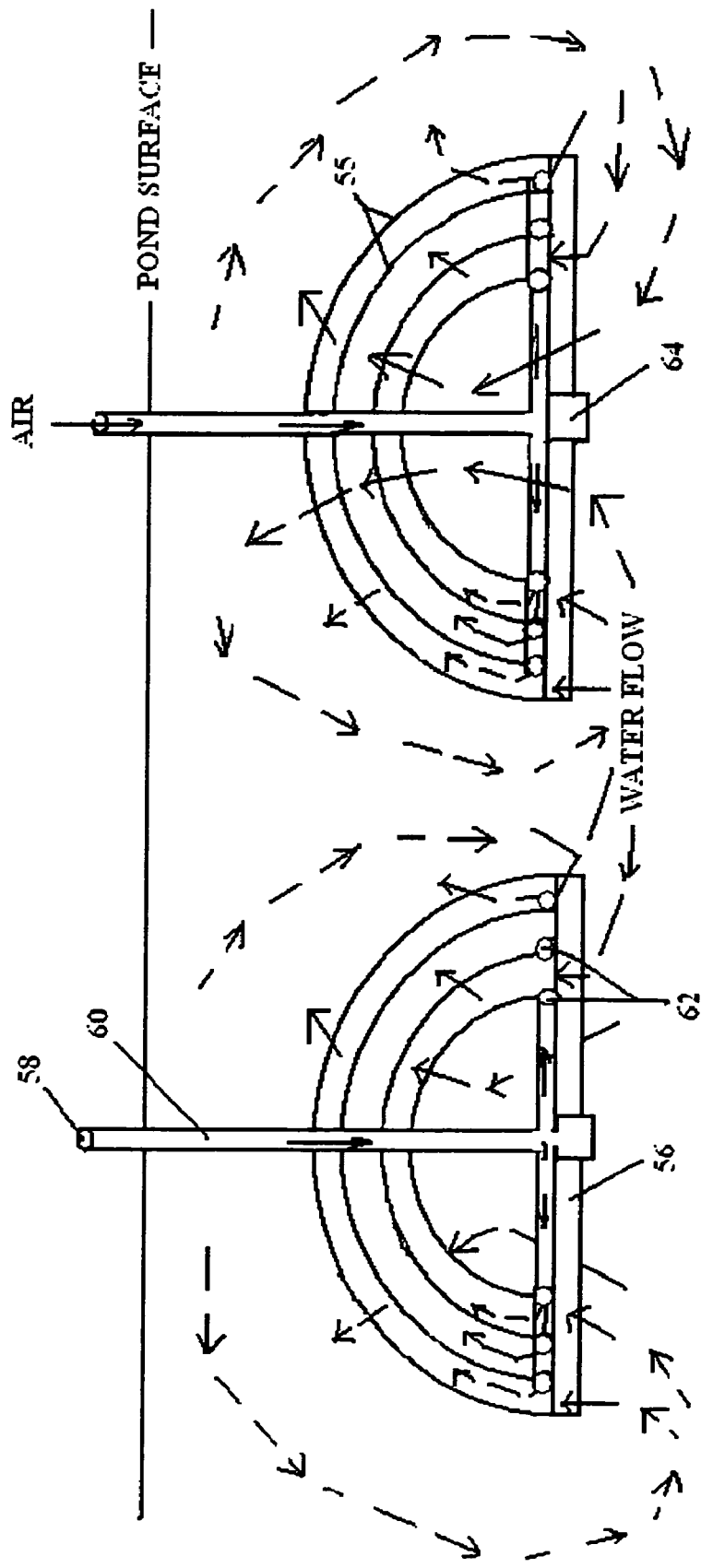
FIG. 2 illustrates an open pond adapted with *Nitrosomonas/Nitrobacter* Bioreactors of FIG. 1

FIG. 2 illustrates an open pond adapted with *Nitrosomonas/Nitrobacter* Bioreactors 54 of FIG. 1. As shown, they comprise two nested opaque half domes 55 impervious to light mounted on a support base 56 at the bottom of an open pond. An air inlet 58 of a central air conduit 60 supports, separates, and interconnects all domes 55 via a circulating air system 62 driven by an air circulating pump 64 to draw in air for circulation between the domes 55 to feed *Nitrosomonas* and *Nitrobacter* bacteria. These bacteria grow on porous high surface area growth intermedia (not shown), which Fill the spaces between the separated half domes to provide surfaces on which the *Nitrosomonas* and *Nitrobacter* bacteria grow and break down ammonia and nitrates/nitrites and BOD compounds as discussed above.

This air circulation system 62 also circulates and draws in water to avoid dead zones in the pond so that the pond nutrients are continually fed into the domes for processing by the *Nitrosomonas* and *Nitrobacter* bacteria. The number of domes is selected based on the treatment removal rates required (based on typical removal rates of 0.42 lbs/day of ammonia and 15 lbs/day of BOD's), and the size of the pond to provide aerobic treatment of all waters contained therein.

In summary, the invention provides a package sulfur dioxide chemical//biological sewage treatment plant and method employing rapid sludge chemical dewatering technology in conjunction chemical precipitation and slower *Nitrosomonas/Nitrobacter* bioreactors 54 to produce treated wastewater suitable for open stream discharge.

Although this specification has made reference to the illustrated embodiments, it is not intended to restrict the scope of the claims. The claims themselves recite those features deemed essential to the invention.

We claim:

1. A treatment method for wastewater streams containing suspended solids and liquids with pathogens, ammonia, nitrates, phosphates and BOD compounds, comprising:
   a. injecting sulfur dioxide into the wastewater streams,
   b. holding the sulfur dioxide-treated wastewater streams for the dwell time required to agglomerate wastewater solids, acid leach any heavy metals from the solids into the wastewater stream liquids, and disinfect the wastewater stream liquids,
   c. separating solids for disposal or reuse from the sulfur dioxide-treated wastewater stream liquids,
   d. pH adjusting the sulfur dioxide-treated wastewater liquids with alkaline reagents, which reduce the biocidal properties of any free $SO_2$, bi-sulfite, and sulfite, and precipitate heavy metals as metal hydroxides, and provide a pH required for *Nitrosomonas* and *Nitrobacter* ammonia and BOD removal treatment,
   e. removing the heavy metal hydroxides by filtration, and
   r. passing the pH adjusted filtered sulfur dioxide-treated wastewater liquids through dark aerated *Nitrosomonas/Nitrobacter* bioreactor containing *Nitrosomonas* and *Nitrobacter* bacteria for the time required to break down and remove the ammonia and nitrate/nitrite and BOD compounds to produce a recovered treated wastewater suitable for open water discharge.

2. A treatment method for wastewater streams according to claim 1 wherein the alkaline reagent is selected to also precipitate phosphates as calcium phosphates or aluminum phosphates, which are removed by filtration along with the metal hydroxides.

3. A treatment method for wastewater streams according to claim 2, wherein the alkaline reagent is selected from the group comprising lime, calcium carbonate, calcium hydroxide, aluminum sulfate and alum.

4. A treatment method for wastewater streams, according to claim 1, wherein the wastewater streams constitute wastewater inflows entering a wastewater treatment plant or treated wastewater resulting from a wastewater treatment plant's processing steps.

5. A treatment method for wastewater streams according to claim 4, wherein the dark aerated *Nitrosomonas/Nitrobacter* bioreactor comprises an open pond containing a series of concentric half domes filled with media continuously aerated with a supply of air moving wastewater streams there through.

6. A treatment method for wastewater streams according to claim 1, wherein separating the solids comprises passing the sulfur dioxide-treated wastewater through acid resistant porous bags with a mesh sized to collect and separate the sulfur dioxide-treated solids from the sulfur dioxide-treated wastewater placed on a drain pad structured to receive filtrate from the drain bags for subsequent use.

7. A treatment method for wastewater streams according to claim 6, wherein the drain pad is movable as needed to treatment locations above flood zones.

8. A treatment method for wastewater stream inflows entering a wastewater treatment plant or treated wastewater resulting from a wastewater treatment plant's processing steps containing suspended solids and liquids with pathogens, ammonia, nitrates, phosphates and BOD compounds, comprising:
   b. injecting sulfur dioxide into the wastewater stream inflows or treated wastewater resulting from a wastewater treatment plant's processing steps,
   c. holding the sulfur dioxide-treated wastewater inflows and streams for the dwell time required to agglomerate wastewater solids, acid leach any heavy metals from the solids into the wastewater stream liquids, and disinfect the wastewater stream liquids,
   d. separating solids for disposal or reuse from the sulfur dioxide-treated wastewater stream liquids,
   e. pH adjusting the sulfur dioxide-treated wastewater liquids with alkaline reagents, which reduce the biocidal properties of any free $SO_2$, bi-sulfite, and sulfite, precipitate heavy metals as metal hydroxides, and precipitate phosphates as calcium phosphates or aluminum phosphates and provide a pH required for *Nitrosomonas* and *Nitrobacter* ammonia and nitrate/nitrite and BOD compound removal,
   f. removing the heavy metal hydroxides, and phosphate precipitates by filtration, and
   g. passing the pH adjusted filtered sulfur dioxide-treated wastewater liquids through dark aerated *Nitrosomonas/Nitrobacter* bioreactor containing *Nitrosomonas* and *Nitrobacter* bacteria for the time required to break down and remove the ammonia and nitrate/nitrite and ROD compounds to produce a recovered treated wastewater suitable for open water discharge.

\* \* \* \* \*